United States Patent [19]

Courtney

[11] Patent Number: 5,376,130
[45] Date of Patent: Dec. 27, 1994

[54] LIMB SUPPORT GARMENT WITH SLIDE FASTENER

[76] Inventor: Charles Courtney, c/o Universal Artificial Limb, 938 Wayne Ave., Silver Spring, Md. 20910

[21] Appl. No.: 101,024
[22] Filed: Aug. 3, 1993
[51] Int. Cl.$^5$ ............................ A61F 2/60; A61F 2/78
[52] U.S. Cl. ............................ 623/33; 24/381; 623/31; 623/32; 623/36
[58] Field of Search .................. 623/32, 35, 36, 31, 623/33; 24/381, 389, 436; 604/345; 2/255, 256, 265, 231

[56] References Cited

U.S. PATENT DOCUMENTS

| | | | |
|---|---|---|---|
| 2,476,513 | 7/1949 | Scott | 604/345 |
| 2,697,833 | 12/1954 | Kaplan | 2/255 |
| 3,005,247 | 10/1961 | Doelter | 24/389 |
| 3,085,569 | 4/1963 | Cook et al. | 24/389 |
| 3,468,310 | 9/1969 | Kimball | 604/345 |
| 4,166,463 | 9/1979 | Bloom | 128/165 |
| 4,628,545 | 12/1986 | Metzler | 2/265 |
| 4,805,601 | 2/1989 | Eischen, Sr. | 128/64 |
| 4,840,635 | 6/1989 | Smith et al. | 623/36 |
| 5,133,752 | 12/1992 | Mandelkern | 623/7 |

FOREIGN PATENT DOCUMENTS 394952A 10/1990 European Pat. Off. ............ 24/389

Primary Examiner—David Isabella
Assistant Examiner—Laura J. Fossum
Attorney, Agent, or Firm—Nikaido, Marmelstein, Muray & Oram

[57] ABSTRACT

An improved support garment for therapeutic compression of a swollen limb. An elastic sock includes a lengthwise slit intermediate the top and bottom, an inelastic pouch bridging the slit for slidably receiving a flat compliant plastic insert, and a slide fastener for opening and closing the slit. Sufficient slack in the pouch allows the fastener to close with the insert in place.

9 Claims, 2 Drawing Sheets

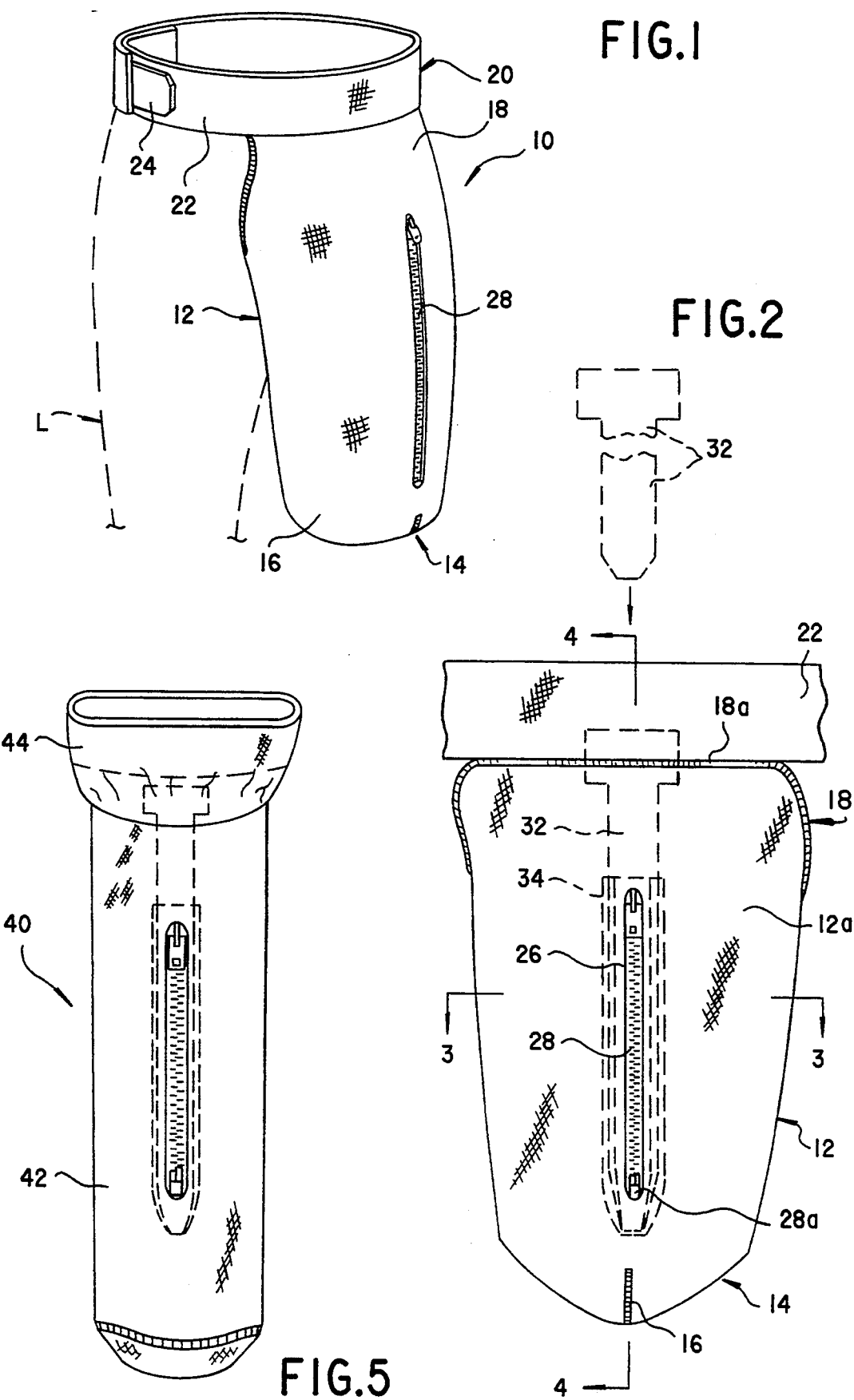

LIMB SUPPORT GARMENT WITH SLIDE FASTENER

BACKGROUND OF THE INVENTION

The present invention relates generally to elastic support garments for limbs of the human body, and more particularly to an improved elastic support garment suitable for therapeutic compression of a swollen limb and for lining a prosthesis.

Elastic support garments are often prescribed for therapeutically reducing swelling of limbs caused by abnormal gravitational accumulation of fluids in the lowermost regions, typically occurring in the residual limb or stump immediately after amputation. They are also used to protect the skin from abrasions due to direct contact with a prothesis or orthopedic appliance.

The garment is usually fabricated of a composite stretch yarn such as a soft filament of rayon or nylon wound about an elastomeric core. U.S. Pat. No. 4,840,635 to Smith et al., for example, discloses a full-fashion knitted stump shrinker sock for therapeutically compressing a residual limb to reduce swelling due to edema.

The sock must fit tightly and firmly over the stump for therapeutic effectiveness. Consequently, the sock can be very difficult to put on, especially by an elderly or handicapped person. According to U.S. Pat. No. 4,166,463 to Bloom, this difficulty is somewhat alleviated by providing a slide fastener lengthwise in the sock. With the fastener open, the sock can be pulled on a swollen limb and then closed tightly and firmly to compress the limb. The fastener must be carefully closed or the sliding element or interlocking teeth may catch on adjacent fabric, chafe sensitive areas of the skin or ensnare cutaneous appendages such as hair or tags. Also, when used as a liner between a residual limb and a prosthesis or orthopedic appliance, areas of the skin compressed under the slide fastener may become irritated under normal activities of the amputee.

SUMMARY OF THE INVENTION

Accordingly, it is an object of the present invention to provide a therapeutic elastic limb support garment which can be put on and removed with relative ease.

Another object is to provide a limb support garment of the type having a longitudinally disposed slide fastener which may be opened and closed tightly without risk of injury to skin contiguous therewith.

Still another object is to provide a therapeutic elastic support garment with a slide fastener suitable for radially compressing distal portions of the residual limb of an amputee.

A further object is to provide an elastic support garment suitable for use as a protective liner and cushion between a prosthesis or orthopedic appliance and the residual limb of an amputee.

A still further object is to provide an elastic support garment which overcomes disadvantages of the prior art, which is of simple construction, and which can be fabricated at comparatively low cost with conventional equipment and materials.

These and other objects of the invention are accomplished by a limb support garment comprising a sock fabricated of a composite stretch yarn with a slit extending lengthwise intermediate the top and bottom ends. The interior of the sock includes an inelastic fabric attached along the entire length of both sides and the bottom of the slit forming thereby a pouch for bridging the slit and for slidably receiving an elongate insert of flat compliant plastic or like material. The slit is opened and closed by a slide fastener in which its interlocking members are fixed to each other at their lower ends. The width of the pouch exceeds the combined widths of the insert and the slit opening required for the sock to be drawn with relative ease over a swollen limb. With the insert installed in the pouch there is sufficient slack remaining in the pouch for the opposite members of the slide fastener to completely interlock and close the slit for radial compression of the limb. When the insert is removed, the pouch provides a protective liner and cushion between the slide fastener and the limb. The sock is applicable to both above- and below-the-knee stumps.

BRIEF DESCRIPTION OF THE DRAWINGS

For a more complete understanding and appreciation of the invention and many of the attendant advantages thereof, reference will be made to the following detailed description taken in conjunction with the accompanying drawings, wherein:

FIG. 1 is a schematic representation in perspective of an above-the-knee elastic limb support garment according to the invention as applied on an amputee;

FIG. 2 is a fragmentary side elevation view of the support garment of FIG. 1 in a relaxed state;

FIG. 5 represents a perspective view of a below-the-knee limb support garment according to the invention.

DETAILED DESCRIPTION OF THE INVENTION

Figure 3:
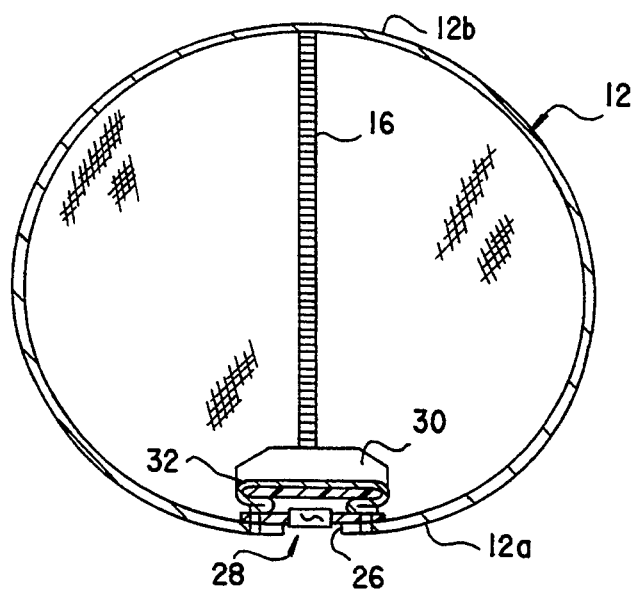
FIG. 3 is a view of the support garment taken in cross section along the line 3—3 of FIG. 2.
Figure 4:
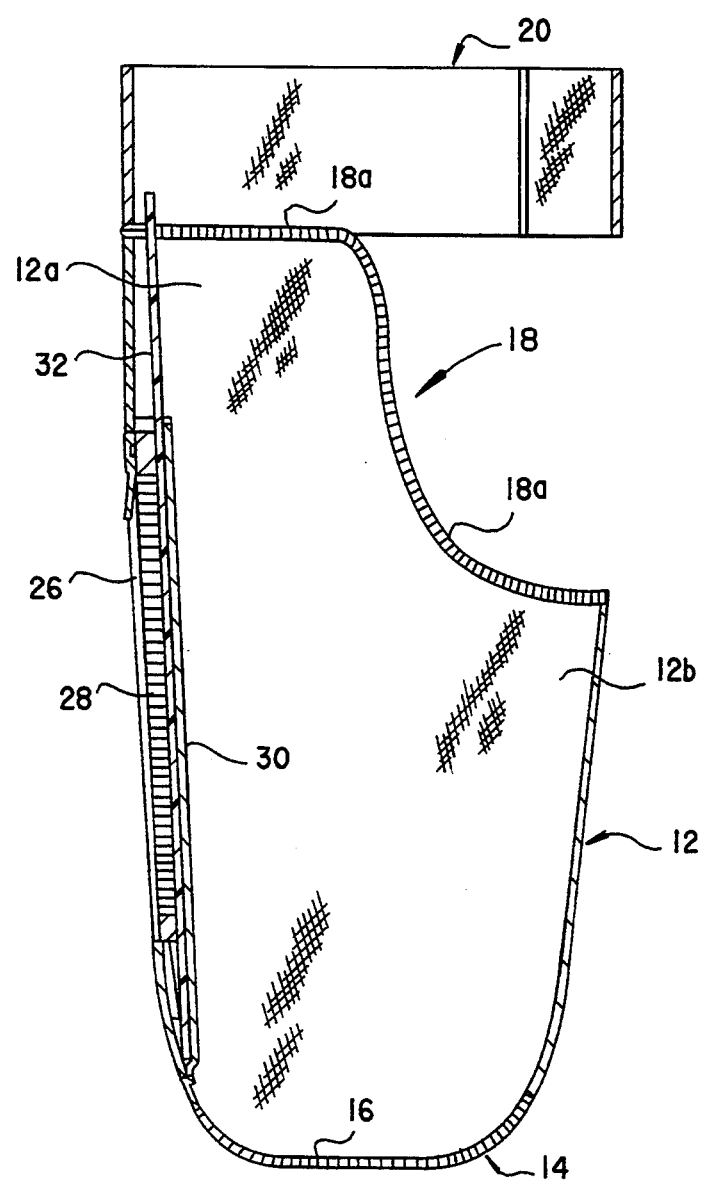
FIG. 4 is a view of the support garment taken in cross section along the line 4—4 of FIG. 2.

Referring to FIG. 1, there is shown an above-the-knee limb support garment, generally indicated by the numeral 10, being worn on a residual left leg L of an amputee. The garment includes a tubular stretchable sock 12 tapered inwardly from an open top end 18 to a bottom end 14 closed by a seam 16. The taper generally conforms to the shape of the residual limb. Referring to FIGS. 2-4, the top of an outer side 12a of the sock is attached along a transverse rim 18a to an adjustable waistband 20. A rim 18b on an inner side 12b is recessed to fit around the groin area of the wearer. Sock 12 is preferably of a single piece of fabric full-fashion knitted from a composite stretch yarn such as a soft filament of rayon, nylon or cotton wound on an elastomeric core such as spandex.

Waistband 20 comprises a belt 22 connected approximately midway along its length to outer side 12a of the sock. The length is sufficient for the ends to overlap on the opposite or right side of the wearer's waist. Belt 22 may be of any of many available stretch or non-stretch materials. The ends are secured in any conventional manner such as by Velcro ® fasteners 24. It will be noted that the garment 10 may be worn as well to a residual right leg of an amputee.

Outer side 12a further includes a slit 26 extending lengthwise intermediate of bottom 14 and top 18 for allowing sock 12 expansion sufficient for donning on a swollen limb with relative ease. A slide fastener such as zipper 28 is attached along the sides of slit 26 with the opposed interlocking teeth joined at the bottom end by stop member 28a.

The interior of sock 12 includes a flexible inelastic panel 30 of flexible fabric or similar material attached along the entire length of slit 26 on both sides and the bottom forming thereby a pouch which spans the slit when zipper 28 opens, and which slideably receives a flat, elongate insert 32 of pliant plastic or like material such as polyethylene or polyproplene. The length 32 is sufficient to extend upwardly from the bottom of pouch 30 to an area within the garment 10, such as near the hip readily accessible to the wearer. The width of the pouch is at least the combined widths of the insert and the maximum expansion of the slit in order that there will be sufficient slack remaining in the pouch for the opposed interlocking teeth of the zipper to engage and close the slit with insert 32 in the pouch.

In use of the garment, sock 12 is drawn over the swollen limb with zipper 28 open in order to allow the sock to expand at slit 26. The distal end of insert 32 is then inserted until it touches the bottom of pouch 30. Using one hand to hold insert 32 in straight alignment with slit 26, the other hand can easily slide element 28b of zipper 28 up to close slit 26 and radially compress the swollen limb.

Insert 32 is intended to be removed during normal wear of the garment, and in its absence the pouch still provides a protective liner and cushion between the zipper and the limb.

FIG. 5 is an alternate embodiment of the limb support garment according to the invention for use on a below the knee residual limb. It comprises a generally tubular sock 42 closed at the bottom and terminating at the top with a flared, standard knit sleeve 42. Slit 260, zipper 280, pouch 300 and insert 320 are substantially the same, structurally and functionally, as in the above-described garment of FIGS. 1–4.

Some of the many advantages and novel features of the invention should now be readily apparent. For example, a therapeutic elastic limb support garment is provided which can be donned and removed with relative ease. A slide fastener opening is provided which can be opened and closed tightly without risk of injury to the skin contiguous therewith, and which enables a swollen residual limb of an amputee to be radially compressed. A elastic support garment with a slide fastener is provided which also serves as a liner and cushion between a residual limb and a prosthesis or other orthopedic appliance. A single garment configuration can be used by amputees with either a right or left leg stump. The garment is of relatively simple construction and can be fabricated at a comparatively low cost with conventional equipment and materials.

It will be understood that various changes in the details, materials, steps and arrangements of parts, which have been herein described and illustrated in order to explain the nature of the invention, may be made by those skilled in the art within the principle and scope of the invention as expressed in the appended claims.

I claim:

1. A stump shrinker comprising:
   an elastic tubular member in a relaxed form approximating a shape of the stump, said tubular member having a longitudinally extending slit intermediate top and bottom ends of said tubular member for providing circumferential expansion of said tubular member;
   a slide fastener secured to opposite sides of said slit for opening and closing said slit;
   an inelastic member having sides secured to said sock along opposite sides and the bottom of said slit forming thereby an internal pouch; and
   a pliant insert slidable in said pouch adjacent to said fastener.

2. A stump shrinker according to claim 1 wherein: the sides of said panel having a minimum width exceeding a width of the insert.

3. A support garment for radially compressing a swollen residual limb of an amputee, comprising:
   an elastic sock having an unstressed shape approximating that of the limb in a non-swollen condition, said sock including a slit extending lengthwise intermediate top and bottom ends of said sock for expansion of said sock when donning on the swollen limb with relative ease;
   a slide fastener having interlocking elements secured to said sock at opposite sides of said slit for opening and closing said slit;
   an elongate inelastic panel having sides secured to an interior of said sock along both sides and a bottom of said slit forming thereby a pouch; and
   an elongate flat insert slidable in said pouch adjacent to said fastener along the entire length thereof.

4. A support garment according to claim 3 wherein: the sides of said panel having a minimum width exceeding a width of the insert.

5. A support garment according to claim 3 further comprising:
   a waistband secured to the top end of said sock, said waistband having free ends of sufficient length for securing to each other on a side of the amputee opposite from said sock.

6. A support garment according to claim 5 wherein: said insert is of a pliant plastic of a length sufficient to extend within said sock from the bottom of said pouch to an area adjacent said waistband.

7. A support garment according to claim 5 wherein: said sock is closed as the bottom end and forms a recessed top end for fitting around a groin area of the amputee.

8. A support garment according to claim 5 further comprising:
   hook and loop fastening means for securing the ends of said waistband.

9. A method of donning an elastic support garment on a residual limb comprising the steps of:
   drawing a tubular sock having an unstressed shaped approximating that of the limb in a non-swollen condition onto the limb, the sock having an open slit extending lengthwise intermediate top and bottom ends of said sock, a slide fastener secured to opposite sides of said slit and longitudinally disposed in the sock and an elongate inelastic panel having sides secured to an interior of said sock along opposite sides and bottom of said slit forming a pouch bridging sides of said slit;
   inserting a flat pliant insert slidable in the pouch adjacent said fastener extending an entire length of the slit;
   holding the insert in place while drawing the slide fastener to close the slit; and
   subsequently removing the insert after the slit has been closed.

* * * * *